United States Patent
El-Sherbeini et al.

(10) Patent No.: US 6,861,516 B1
(45) Date of Patent: Mar. 1, 2005

(54) **MRAY GENE AND ENZYME OF *PSEUDOMONAS AERUGINOSA***

(75) Inventors: Mohamed El-Sherbeini, Westfield, NJ (US); Barbara A. Azzolina, Denville, NJ (US)

(73) Assignee: Merck & Co., Inc., Rahway, NJ (US)

(*) Notice: Subject to any disclaimer, the term of this patent is extended or adjusted under 35 U.S.C. 154(b) by 99 days.

(21) Appl. No.: 10/089,787

(22) PCT Filed: Sep. 29, 2000

(86) PCT No.: PCT/US00/27056

§ 371 (c)(1),
(2), (4) Date: Apr. 3, 2002

(87) PCT Pub. No.: WO01/25251

PCT Pub. Date: Apr. 12, 2001

Related U.S. Application Data

(60) Provisional application No. 60/157,580, filed on Oct. 4, 1999.

(51) Int. Cl.$^7$ ........................ C07H 21/04; C12N 15/00; C12N 15/74
(52) U.S. Cl. .................... 536/23.7; 435/320.1; 435/471
(58) Field of Search ............................. 536/23.7, 23.1; 435/320.1, 69.1, 253.3, 325, 6, 471

(56) References Cited

U.S. PATENT DOCUMENTS 6,551,795 B1    4/2003  Rubenfield et al. ......... 435/69.1

FOREIGN PATENT DOCUMENTS

| EP | 897 007 | 2/1999 |
| WO | WO 96/40893 | 12/1996 |
| WO | WO 98/18931 | 5/1998 |
| WO | WO 99/61050 | 12/1999 |
| WO | WO 01/70955 | 9/2001 |

OTHER PUBLICATIONS

Genbank Accession No. AB007500, Wada, A., et al. "Penicillin–binding protein 1 of Staphylocotcus aureus is essential for growth".
Genbank Accession No. AF034153, El–Sherbeini, M. et al. "Cloning and characterization of the Staphylococcus aureus mraY gene encoding Phospho–N–Acetylmuramoyl–Pentapeptide Translocase".
Genbank Accession No. U94706, Pucci, M.J., et al. "Identification and characterization of cell wall–cell division gene clusters in pathogenic gram–positive cocci".
Bouhss, Ahmed et al. "Topological analysis of the MraY protein catalysing the first membrane step of peptidoglycan synthesis". Molecular Microbiology, (1999), 34(3), pp. 576–585.
Boyle, David et al. "mraY Is an Essential Gene for Cell Growth in *Escherichia coli*". Journal of Bacteriology, Dec. (1998), pp. 6429–6432.

Azzolina, Barbara et al. "The Cell abd Cell Division Gene Cluster in the Mra Operon of Pseudomonas aeruginosa: Cloning, Production, and Purification of Active Enzymes". Protein Expression and Purification, (2001), 21, pp. 393–400.
Brandish, Philip et al. "Slow Binding Inhibition of Phospho–N–acetylmuramyl–pentapeptide–translocase (*Escherichia coli*) by Mureidomycin A*". The Journal of Biological Chemistry, (1996), vol. 271, No. 13, pp. 7609–7614.
Bugg, T.D.H. et al. "Intracellular Steps of Bacterial Cell Wall Peptidoglycan Biosynthesis: Enzymology, Antibiotics, and Antibiotic Resistance". Natural Product Reports, (1992), pp. 199–215.
El–Sherbeini, Mohamed et al. "Cloning and expression of Staphylococcus aureus and Streptococcus pyogenes murD genes encoding uridine diphosphate N–acetylmuramoyl–L–alanine:D–gluatamate ligases". Gene, (1998), 210, pp. 117–125.
Ikeda, Masato et al. "The *Escherichia coli* mraY Gene Encoding UDP–N–Acetylmuramoyl–Pentapeptide: Undecaprenyl–Phosphate Phospho–N–Acetylmuramoyl–Pentapeptide Transferase". Journal of Bacteriology, (1991), pp. 1021–1026.
Inukai, Masatoshi et al. "Selective Inhibition of the Bacterial Translocase Reaction in Peptidoglycan Synthesis by Mureidomycin". Antimicrobial Agents and Chemotherapy, (1993), pp. 980–983.
Liao, Xiaowen et al. "Physical mapping of 32 genetic markers on the Pseudomonas aeruginosa PAO1 chromosome", Microbiology, (1996), 142, pp. 79–86.
Pless, Dorothy D. et al. "Initial Membrane Reaction in Peptidoglycan Synthesis". The Journal of Biological Chemistry, (1973), vol. 248, No. 5, pp. 1568–1576.
Pucci, Michael et al. "Identification and Characterization of Cell Wall–Cell Division Gene Clusters in Pathogenic Gram–Positive Cocci". Journal of Bacteriology, (1997), pp. 5632–5635.
"Biosynthesis peptidoglycan". Microbial Cell Walls and Membranes, H.J. Rogers et al., eds. (London: Chapman and Hall), (1980), pp. 238–296.
Schmidt, Karen et al. "Comparitive Genome Mapping of Pseudomonas aeruginosa PAO with P. aeruginosa C, Which Belongs to a Major Clone in Cystic Fibrosis Patients and Aquatic Habitats". Journal of Bacteriology, (1996), pp. 85–93.
Stover, C.K. et al. "Complete genome sequence of Pseudomonas aeruginosa PA01, an opportunistic pathogen", Nature, (2000), vol. 406, p. 959–964.
Wada, Akihito et al. "Penicillin–Binding Protein 1 of Staphylococcus aureus Is Essential for Growth". Journal of Bacteriology, (1998), pp. 2759–2765.

*Primary Examiner*—S. Devi
(74) *Attorney, Agent, or Firm*—Patricia L. Chisholm; Jack L. Tribble

(57) ABSTRACT

Polynucleotides and polypeptides of *Pseudomonas aeruginosa* MraY, an enzyme involved in bacterial cell wall biosynthesis, are provided. The recombinant MraY enzyme is catalytically active in the first step of the membrane cycle of peptidoglycan biosynthesis. Also provided are proteins encoded by the sequences, host cells expressing the recombinant enzyme, and probes and primers.

3 Claims, 1 Drawing Sheet

```
   1 atgctcctgctgctggccgaatacctgcaacagttctacaagggcttcggcgtcttccag    60
     MetLeuLeuLeuLeuAlaGluTyrLeuGlnGlnPheTyrLysGlyPheGlyValPheGln 61 tacctgaccctgcgcggcattctcagcgtgctcaccgcgctgtcgctgtcgctgtggctg   120
     TyrLeuThrLeuArgGlyIleLeuSerValLeuThrAlaLeuSerLeuSerLeuTrpLeu 121 gggccctggatgatccgtaccttgcagatccccagatcggccaggccgtgcgcaacgac   180
     GlyProTrpMetIleArgThrLeuGlnIleProGlnIleGlyGlnAlaValArgAsnAsp 181 ggtccgcagtcgcacctgtcgaagaagggcacccccgaccatgggcggcgccctgatcctt   240
     GlyProGlnSerHisLeuSerLysLysGlyThrProThrMetGlyGlyAlaLeuIleLeu 241 accgccatagccatcagcacgctgctgtgggcggatctttccaaccgctacgtgtgggta   300
     ThrAlaIleAlaIleSerThrLeuLeuTrpAlaAspLeuSerAsnArgTyrValTrpVal 301 gtgctggtcgttaccctgctgttcggtgccatcggctgggtagacgactaccgcaaggtg   360
     ValLeuValValThrLeuLeuPheGlyAlaIleGlyTrpValAspAspTyrArgLysVal 361 atcgagaagaactcccgtggcctgccgagccgctggaagtacttctggcagtcggtgttc   420
     IleGluLysAsnSerArgGlyLeuProSerArgTrpLysTyrPheTrpGlnSerValPhe 421 ggcatcggcgccgccgtgttcctctacatgactgccgaaaccccgatcgagaccaccctg   480
     GlyIleGlyAlaAlaValPheLeuTyrMetThrAlaGluThrProIleGluThrThrLeu 481 atcgtgccgatgctgaagagcgtcgagatccagttgggcatcttcttcgtggtcctgacc   540
     IleValProMetLeuLysSerValGluIleGlnLeuGlyIlePhePheValValLeuThr 541 tacttcgtcatcgtcggctcgagcaatgcggtgaacctcaccgacggtctcgacggcctg   600
     TyrPheValIleValGlySerSerAsnAlaValAsnLeuThrAspGlyLeuAspGlyLeu 601 gcgatcatgccgacggtaatggttgccggcgcgctgggcatcttctgctacctgtcgggc   660
     AlaIleMetProThrValMetValAlaGlyAlaLeuGlyIlePheCysTyrLeuSerGly 661 aacgtgaagttcgccgagtacctgctgattcccaacgtaccgggcgccggcgagctgatc   720
     AsnValLysPheAlaGluTyrLeuLeuIleProAsnValProGlyAlaGlyGluLeuIle 721 gtgttctgcgccgcgctggtcggcgccggcctcggcttcctctggttcaacacctatccg   780
     ValPheCysAlaAlaLeuValGlyAlaGlyLeuGlyPheLeuTrpPheAsnThrTyrPro 781 gcgcaggtcttcatgggcgacgtcggcgcgctggcgctgggcgccgcgctgggcaccatc   840
     AlaGlnValPheMetGlyAspValGlyAlaLeuAlaLeuGlyAlaAlaLeuGlyThrIle 841 gcggtgatcgtgcgccaggagatcgtgctgttcatcatgggtggggtgttcgtcatggaa   900
     AlaValIleValArgGlnGluIleValLeuPheIleMetGlyGlyValPheValMetGlu 901 accctctcggtgatgatccaggtcgcttccttcaagctgaccggacgccgcgtcttccgt   960
     ThrLeuSerValMetIleGlnValAlaSerPheLysLeuThrGlyArgArgValPheArg 961 atggcgccgatccatcaccatttcgaactgaaaggctggccggacccgcgcgtgatcgtg  1020
     MetAlaProIleHisHisHisPheGluLeuLysGlyTrpProAspProArgValIleVal 1021 cgcttctggatcatcaccgtgatcctggtgctgatcggcctcgccaccttgaagctgcgt  1080
     ArgPheTrpIleIleThrValIleLeuValLeuIleGlyLeuAlaThrLeuLysLeuArg 1081 tga                                                            1140
     ***
```

FIG.1

SEQUENCE LISTING

<160> NUMBER OF SEQ ID NOS: 4

<210> SEQ ID NO 1
<211> LENGTH: 1083
<212> TYPE: DNA
<213> ORGANISM: Pseudomonas Aeruginosa

<400> SEQUENCE: 1
atgctcctgc tgctggccga ataccugcaa cagttctaca agggcttcgg cgtcttccag      60
tacctgaccc tgcgcggcat tctcagcgtg ctcaccgcgc tgtcgctgtc gctgtggctg     120
gggccctgga tgatccgtac cttgcagatc ccccagatcg gccaggccgt gcgcaacgac     180

```
ggtccgcagt cgcacctgtc gaagaagggc accccgacca tgggcggcgc cctgatcctt      240
accgccatag ccatcagcac gctgctgtgg gcggatcttt ccaaccgcta cgtgtgggta      300
gtgctggtcg ttaccctgct gttcggtgcc atcggctggg tagacgacta ccgcaaggtg      360
atcgagaaga actcccgtgg cctgccgagc cgctggaagt acttctggca gtcggtgttc      420
ggcatcggcg ccgccgtgtt cctctacatg actgccgaaa ccccgatcga gaccaccctg      480
atcgtgccga tgctgaagag cgtcgagatc cagttgggca tcttcttcgt ggtcctgacc      540
tacttcgtca tcgtcggctc gagcaatgcg gtgaacctca ccgacggtct cgacggcctg      600
gcgatcatgc cgacggtaat ggttgccggc gcgctgggca tcttctgcta cctgtcgggc      660
aacgtgaagt tcgccgagta cctgctgatt cccaacgtac cgggcgccgg cgagctgatc      720
gtgttctgcg ccgcgctggt cggcgccggc ctcggcttcc tctggttcaa cacctatccg      780
gcgcaggtct tcatgggcga cgtcggcgcg ctggcgctgg gcgccgcgct gggcaccatc      840
gcggtgatcg tgcgccagga gatcgtgctg ttcatcatgg gtgggtgtt cgtcatggaa       900
accctctcgg tgatgatcca ggtcgcttcc ttcaagctga ccggacgccg cgtcttccgt      960
atggcgccga tccatcacca tttcgaactg aaaggctggc cggacccgcg cgtgatcgtg     1020
cgcttctgga tcatcaccgt gatcctggtg ctgatcggcc tcgccacctt gaagctgcgt     1080
tga                                                                    1083

<210> SEQ ID NO 2
<211> LENGTH: 360
<212> TYPE: PRT
<213> ORGANISM: Pseudomonas Aeruginosa

<400> SEQUENCE: 2

Met Leu Leu Leu Leu Ala Glu Tyr Leu Gln Gln Phe Tyr Lys Gly Phe
 1               5                  10                  15
Gly Val Phe Gln Tyr Leu Thr Leu Arg Gly Ile Leu Ser Val Leu Thr
                20                  25                  30
Ala Leu Ser Leu Ser Leu Trp Leu Gly Pro Trp Met Ile Arg Thr Leu
            35                  40                  45
Gln Ile Pro Gln Ile Gly Gln Ala Val Arg Asn Asp Gly Pro Gln Ser
        50                  55                  60
His Leu Ser Lys Lys Gly Thr Pro Thr Met Gly Gly Ala Leu Ile Leu
    65                  70                  75                  80
Thr Ala Ile Ala Ile Ser Thr Leu Leu Trp Ala Asp Leu Ser Asn Arg
                85                  90                  95
Tyr Val Trp Val Val Leu Val Thr Leu Leu Phe Gly Ala Ile Gly
                100                 105                 110
Trp Val Asp Asp Tyr Arg Lys Val Ile Glu Lys Asn Ser Arg Gly Leu
            115                 120                 125
Pro Ser Arg Trp Lys Tyr Phe Trp Gln Ser Val Phe Gly Ile Gly Ala
        130                 135                 140
Ala Val Phe Leu Tyr Met Thr Ala Glu Thr Pro Ile Glu Thr Thr Leu
145                 150                 155                 160
Ile Val Pro Met Leu Lys Ser Val Glu Ile Gln Leu Gly Ile Phe Phe
                165                 170                 175
Val Val Leu Thr Tyr Phe Val Ile Gly Ser Ser Asn Ala Val Asn
                180                 185                 190
Leu Thr Asp Gly Leu Asp Gly Leu Ala Ile Met Pro Thr Val Met Val
            195                 200                 205
```

-continued

```
Ala Gly Ala Leu Gly Ile Phe Cys Tyr Leu Ser Gly Asn Val Lys Phe
    210                 215                 220
Ala Glu Tyr Leu Leu Ile Pro Asn Val Pro Gly Ala Gly Glu Leu Ile
225                 230                 235                 240
Val Phe Cys Ala Ala Leu Val Gly Ala Gly Leu Gly Phe Leu Trp Phe
                245                 250                 255
Asn Thr Tyr Pro Ala Gln Val Phe Met Gly Asp Val Gly Ala Leu Ala
                260                 265                 270
Leu Gly Ala Ala Leu Gly Thr Ile Ala Val Ile Val Arg Gln Glu Ile
            275                 280                 285
Val Leu Phe Ile Met Gly Gly Val Phe Val Met Glu Thr Leu Ser Val
    290                 295                 300
Met Ile Gln Val Ala Ser Phe Lys Leu Thr Gly Arg Arg Val Phe Arg
305                 310                 315                 320
Met Ala Pro Ile His His His Phe Glu Leu Lys Gly Trp Pro Asp Pro
                325                 330                 335
Arg Val Ile Val Arg Phe Trp Ile Ile Thr Val Ile Leu Val Leu Ile
                340                 345                 350
Gly Leu Ala Thr Leu Lys Leu Arg
            355                 360

<210> SEQ ID NO 3
<211> LENGTH: 29
<212> TYPE: DNA
<213> ORGANISM: Artificial Sequence
<220> FEATURE:
<223> OTHER INFORMATION: PCR Primer

<400> SEQUENCE: 3
ttcatatgct cctgctgctg gccgaatac                                    29

<210> SEQ ID NO 4
<211> LENGTH: 27
<212> TYPE: DNA
<213> ORGANISM: Artificial Sequence
<220> FEATURE:
<223> OTHER INFORMATION: PCR Primer

<400> SEQUENCE: 4
ttggatcctc aacgcagctt caaggtg                                      27
```

MRAY GENE AND ENZYME OF *PSEUDOMONAS AERUGINOSA*

CROSS-REFERENCE TO RELATED APPLICATIONS

This application is a national stage §371 application of PCT/US00/27056 filed Sep. 29, 2000, and claims priority to provisional application 60/157,580 filed in the United States on Oct. 4, 1999.

STATEMENT REGARDING FEDERALLY-SPONSORED R&D

Not Applicable

REFERENCE TO MICROFICHE APPENDIX

Not Applicable

FIELD OF THE INVENTION

This invention relates to the genes and enzymes involved in cell wall synthesis in bacteria.

BACKGROUND OF THE INVENTION

The pathway of peptidoglycan (PG) biosynthesis is both essential and unique to bacteria and the responsible enzymes are present in both Gram-negative and Gram-positive bacteria. Thus, inhibitors of these enzymes are likely to be broad spectrum and safe antibiotics. In fact, several enzymes in this pathway are molecular targets of naturally occurring antibiotics such as fosfomycin, cycloserine, β-lactams and vancomycin (Bugg & Walsh, 192 Nat. Prod. Rep. 9:199–215).

One enzyme intrinsic to the peptidoglycan biosynthesis is MraY. To date, no MraY sequences have been disclosed for *Pseudomonas aeruginosa*, an opportunistic pathogen causing infections in patients with burns or neutropenia. More serious is its involvement in respiratory tracts of cystic fibrosis patients.

It would be desirable to have polynucleotides and polypeptides encoding the MraY protein of *Pseudomonas aeruginosa* in order to further screen compounds for antibiotic activity against this enzyme catalytically active in the first step of the membrane cycle of peptidoglycan biosynthesis. Inhibitors of this enzyme would be particularly helpful in preventing the growth of *Pseudomonads* and other G+C rich bacteria.

Possession of this information would also greatly facilitate determinations as to the role of the encoded enzyme, Phospho-N-Acetylmurmoyl-Pentapeptide-Translocase, in the pathogenesis of infection and disease.

SUMMARY OF THE INVENTION

Polynucleotides and polypeptides of *Pseudonmonas aeruginosa* MraY, an enzyme involved in bacterial cell wall biosynthesis, are provided. The recombinant MraY enzyme is catalytically active in the first step of the membrane cycle of peptidoglycan biosynthesis, transferring the N-acetylmuramic acid pentapeptide to a bactoprenol phosphate carrier molecule. The enzyme is useful in in vitro assays to screen for antibacterial compounds that target cell wall biosynthesis. The invention includes the polynucleotides, proteins encoded by the polynucleotides, and host cells expressing the recombinant enzyme, probes and primers, and the use of these molecules in assays.

An aspect of this invention is an isolated polynucleotide having a sequence encoding a *Pseudomonas aeruginosa* MraY protein, or a complementary sequence. In a particular embodiment the encoded protein has a sequence corresponding to SEQ ID NO:2. In preferred embodiments the polynucleotide can be DNA, RNA or a mixture of both, and can be single or double stranded. In a most preferred embodiment, the polynucleotide has a sequence shown in SEQ ID NO:1.

An aspect of this invention is a probe having a sequence of at least about 25 contiguous nucleotides that is specific for a naturally occurring polynucleotide encoding a *Pseudomonas aeruginosa* MraY protein. Probes in accordance with this description are useful for the specific detection of the presence of a polynucleotide encoding a *Pseudomonas aeruginosa* MraY protein. In preferred embodiments, the probes of this aspect can have additional components including, but not limited to, compounds, isotopes, proteins or sequences for ready detection.

An aspect of this invention is a primer having a sequence of at least about 25 contiguous nucleotides that is specific for a naturally occurring polynucleotide encoding a *Pseudomonas aeruginosa* MraY protein. Primers in accordance with this description are useful in nucleic acid amplification-based assays for the specific detection of the presence of a polynucleotide encoding a *Pseudonmonas aeruginosa* MraY protein. In preferred embodiments, the primers of this aspect can have additional components including, but not limited to, compounds, isotopes, proteins or sequences for ready detection.

An aspect of this invention is an expression vector including a polynucleotide encoding a *Pseudomonas aeruginosa* MraY protein, or a complementary sequence, and regulatory regions. In a particular embodiment the encoded protein has a sequence corresponding to SEQ ID NO:2. In particular embodiments, the vector can have any of a variety of regulatory regions known and used in the art as appropriate for the types of host cells the vector can be used in. In a most preferred embodiment, the vector has regulatory regions appropriate for the expression of the encoded protein in gram-negative prokaryotic host cells. In other embodiments, the vector has regulatory regions appropriate for expression of the encoded protein in gram-positive host cells, yeasts, cyanobacteria or actinomycetes. In some preferred embodiments the regulatory regions provide for inducible expression while in other preferred embodiments the regulatory regions provide for constitutive expression. Finally, according to this aspect, the expression vector can be derived from a plasmid, phage, virus or a combination thereof.

An aspect of this invention is a host cell comprising an expression vector including a polynucleotide encoding a *Pseudomonas aeruginosa* MraY protein, or a complementary sequence, and regulatory regions. In a particular embodiment the encoded protein has a sequence corresponding to SEQ ID NO:2. In preferred embodiments, the host cell is a yeast, gram-positive bacterium, cyanobacterium or actinomycete. In a most preferred embodiment, the host cell is a gram-negative bacterium.

An aspect of this invention is a process for expressing a MraY protein of *P. aeruginosa* in a host cell. In this aspect a host cell is transformed or transfected with an expression vector including a polynucleotide encoding a *Pseudomonas aeruginosa* MraY protein, or a complementary sequence. According to this aspect, the host cell is cultured under conditions conducive to the expression of the encoded MraY protein. In particular embodiments the expression is inducible or constitutive. In a particular embodiment the encoded protein has a sequence corresponding to SEQ ID NO:2.

An aspect of this invention is a purified polypeptide having an amino acid sequence of SEQ ID NO:2. Cellular extracts comprising a polypeptide having the above amino acid sequence are also included within the instant invention.

BRIEF DESCRIPTION OF THE DRAWINGS

FIG. 1. Nucleotide sequence (SEQ ID NO:1) and the predicted amino acid sequence (SEQ ID NO:2) of *P. aeruginosa* MraY. The amino acid sequence (SEQ ID NO:2) is presented in a three-letter code below the nucleotide sequence (nucleotides 34 to 1113 of SEQ ID NO:1).

DETAILED DESCRIPTION OF THE INVENTION

This invention provides polynucleotides and polypeptides of a cell wall biosynthesis gene from *Pseudomonas aeruginosa*, referred to herein as MraY. The polynucleotides and polypeptides are used to further provide expression vectors, host cells comprising the vectors, probes and primers, and assays for the presence or expression of MraY.

Bacterial mraY encodes for phoshpo-N-acetylmuramoyl-pentapeptide translocase, an enzyme responsible for catalyzing the first step of the membrane cycle of peptidoglycan biosynthesis, transfer of the N-acetylmuramic acid pentapeptide to a bactoprenol phosphate carrier molecule.

The mraY gene was cloned from *Pseudomonas aeruginosa*. Sequence analysis of the *P. aeruginosa* mraY gene revealed an open reading frame of 361 amino acids.

Nucleic acids encoding MraY from *Pseudomonas aeruginosa* are useful in the expression and production of the *P. aeruginosa* MraY protein. The nucleic acids are also useful in providing probes for detecting the presence of *P. aeruginosa* MraY.

As used herein, the following definitions apply:

The term "about" in the specification means within approximately 10–20% greater or lesser than particularly stated.

The term "polynucleotide" means a nucleic acid of more than one nucleotide. A polynucleotide can be made up of multiple polynucleotide units that are referred to by description of the unit. For example, a polynucleotide can comprise within its bounds a polynucleotide(s) having a coding sequence(s), a polynucleotide(s) that is a regulatory region (s) and/or other polynucleotide units commonly used in the art.

The term "expression vector" means a polynucleotide having regulatory regions operably linked to a coding region such that, when in a host cell, the regulatory regions can direct the expression of the coding sequence. The use of expression vectors is well known in the art. Expression vectors can be used in a variety of host c ells and, therefore, the regulatory regions are preferably chosen as appropriate for the particular host cell.

The term "regulatory region" means a polynucleotide that can promote or enhance the initiation or termination of transcription or translation of a coding sequence. A regulatory region includes a sequence that is recognized by the RNA polymerase, ribosome, or associated transcription or translation initiation or termination factors of a host cell. Regulatory regions that direct the initiation of transcription or translation can direct constitutive or inducible expression of a coding sequence.

The terms "purified" and "isolated" are utilized interchangeably to stand for the proposition that the polynucleotide, protein and polypeptide, or respective fragments thereof in question have been removed from the in vivo environment so that they exist in a form or purity not found in nature. This, however, is not mandated of cDNA as understood by one of ordinary skill in the art.

The term "substantially pure" with regard to a polynucleotide means it is obtained purified from cellular components by standard methods at a concentration of at least about 100-fold higher than that found in nature. A polynucleotide is considered essentially pure if it is obtained at a concentration of at least about 1000-fold higher than that found in nature.

Polynucleotides

Polynucleotides useful in the present invention include those described herein and those that one of skill in the art will be able to derive therefrom following the teachings of this specification.

An aspect of the present invention is a polynucleotide encoding a MraY protein of *Pseudomonas aeruginosa*. It is known that there is a substantial amount of redundancy in the various codons which code for specific amino acids. Therefore, this invention is also directed to those DNA sequences that encode RNA comprising alternative codons which code for the eventual translation of the identical amino acid. The present invention, thus, discloses codon redundancy which can result in different DNA molecules encoding an identical protein. For purposes of this specification, a sequence bearing one or more replaced codons will be defined asa degenerate variation.

A further aspect of the present invention is a cDNA encoding a MraY protein of *Pseudomonas aeruginosa*.

A preferred aspect of the present invention is an isolated nucleic acid encoding a MraY protein of *Pseudomonas aeruginosa*. A preferred embodiment is a nucleic acid having the sequence disclosed in FIG. 1, SEQ ID NO:1.

The isolated nucleic acid molecule of the present invention can include a ribonucleic or deoxyribonucleic acid molecule, which can be single (coding or noncoding strand) or double stranded, as well as synthetic nucleic acid, such as a synthesized, single stranded polynucleotide.

Noncoding or antisense strands can be useful as modulators of the gene by interacting with RNA encoding the MraY protein. Antisense strands are preferably less than full length strands having sequences unique or specific for RNA encoding the polypeptide.

Also included in the present invention are polynucleotides that hybridize to *P. aeruginosa* mraY sequences under stringent conditions. By way of example, and not limitation, a procedure using conditions of high stringency is as follows: Prehybridization of filters containing DNA is carried out for 2 hr. to overnight at 65° C. in buffer composed of 6×SSC, 5× Denhardt's solution, and 100 µg/ml denatured salmon sperm DNA. Filters are hybridized for 12 to 48 hrs at 65° C. in prehybridization mixture containing 100 µl/ml denatured salmon sperm DNA and 5–20×10$^6$ cpm of $^{32}$P-labeled probe. Washing of filters is done at 37° C. for 1 hr in a solution containing 2×SSC, 0.1% SDS. This is followed by a wash in 0.1×SSC, 0.1% SDS at 50° C. for 45 min. before autoradiography.

Other procedures using conditions of high stringency would include either a hybridization step carried out in 5×SSC, 5× Denhardt's solution, 50% formamide at 42° C. for 12 to 48 hours or a washing step carried out in 0.2×SSPE, 0.2% SDS at 65° C. for 30 to 60 minutes.

Reagents mentioned in the foregoing procedures for carrying out high stringency hybridization are well known in the art. Details of the composition of these reagents can be found in, e.g., Sambrook, el al., 1989, Molecular Cloning: A Laboratory Manual, second edition, Cold Spring Harbor Laboratory Press. In addition to the foregoing, other conditions of high stringency which may be used are well known in the art.

Polypeptides

A preferred aspect of the present invention is a substantially purified form of the MraY protein from *Pseudomonas aeruginosa*. A preferred embodiment is a protein that has the amino acid sequence which is shown in FIG. 1, in SEQ ID NO:2.

Probes and Primers

Probes comprising full length or partial sequences of SEQ ID NO:1 can be used to determine whether a cell or sample contains *P. aeruginosa* mraY DNA or RNA. A preferred probe is a single stranded antisense probe having at least the full length of the coding sequence of MraY. It is also preferred to use probes that have less than the full length sequence, and contain sequences specific for *P. aeruginosa* mraY DNA or RNA. The identification of a sequence(s) for use as a specific probe is well known in the art and involves choosing a sequence(s) that is unique to the target sequence, or is specific thereto. It is preferred that probes have at least about 25 nucleotides, more preferably about 30 to 35 nucleotides. The longer probes are believed to be more specific for *P. aeruginosa* mraY gene(s) and RNAs and can be used under more stringent hybridization conditions. Longer probes can be used but can be more difficult to prepare synthetically, or can result in lower yields from synthesis.

Examples of sequences that are useful as probes or primers for *P. aeruginosa* mraY gene(s) are Primer A (sense) 5'-T CAT ATG CTC CTG CTG CTG GCC GAA TAC-3' (SEQ ID NO:3) and Primer B (antisense) 5'-TT GGA TCC TCA ACG CAG CTT CAA GGT G-3' (SEQ ID NO:4). Restriction sites, underlined, for NdeI and BamHI are added to the 5' ends of the primers to allow cloning between the NdeI and BamHI sites of the expression vector pET-11a. However, one skilled in the art will recognize that these are only a few of the useful probe or primer sequences that can be derived from SEQ ID NO:1.

Polynucleotides having sequences that are unique or specific for *P. aeruginosa* MraY can be used as primers in amplification reaction assays. These assays can be used in tissue typing as described herein. Additionally, amplification reactions employing primers derived from *P. aeruginosa* MraY sequences can be used to obtain amplified *P. aeruginosa* mraY DNA using the mraY DNA of the cells as an initial template. Many types of amplification reactions are known in the art and include, without limitation, Polymerase Chain Reaction, Reverse Transcriptase Polymerase Chain Reaction, Strand Displacement Amplification and Self-Sustained Sequence Reaction. Any of these or like reactions can be used with primers derived from SEQ ID NO:11.

Expression of MraY

A variety of expression vectors can be used to express recombinant MraY in host cells. Expression vectors are defined herein as nucleic acid sequences that include regulatory sequences for the transcription of cloned DNA and the translation of their mRNAs in an appropriate host. Such vectors can be used to express a bacterial gene in a variety of hosts such as bacteria, bluegreen algae, plant cells, insect cells and animal cells. Specifically designed vectors allow the shuttling of genes between hosts such as bacteria-yeast or bacteria-animal cells. An appropriately constructed expression vector should contain: an origin of replication for autonomous replication in host cells, selectable markers, a limited number of useful restriction enzyme sites, a potential for high copy number, and regulatory sequences. Expression vectors can include, but are not limited to, cloning vectors, modified cloning vectors, specifically designed plasmids or viruses.

In particular, a variety of bacterial expression vectors can be used to express recombinant MraY in bacterial cells. Commercially available bacterial expression vectors which are suitable for recombinant MraY expression include, but are not limited to pQE (QIAGEN), pET11a (NOVAGEN), lambda gt11 (INVITROGEN), and pKK223-3 PHARMACIA).

Alternatively, one can express mraY DNA in cell-free transcription-translation systems, or mraY RNA in cell-free translation systems. Cell-free synthesis of MraY can be in batch or continuous formats known in the art.

One can also synthesize MraY chemically, although this method is not preferred.

A variety of host cells can be employed with expression vectors to synthesize MraY protein. These can include *E. coli, Bacillus*, and *Salmonella*. Insect and yeast cells can also be appropriate.

Following expression of MraY in a host cell, MraY polypeptides can be recovered. Several protein purification procedures are available and suitable for use. MraY protein and polypeptides can be purified from cell lysates and extracts, or from culture medium, by various combinations of, or individual application of methods including ultrafiltration, acid extraction, alcohol precipitation, salt fractionation, ionic exchange chromatography, phosphocellulose chromatography, lecithin chromatography, affinity (e.g., antibody or His-Ni) chromatography, size exclusion chromatography, hydroxylapatite adsorption chromatography and chromatography based on hydrophobic or hydrophillic interactions. In some instances, protein denaturation and refolding steps can be employed. High performance liquid chromatography (HPLC) and reversed phase HPLC can also be useful. Dialysis can be used to adjust the final buffer composition.

The following examples are presented in order to illustrate the instant invention.

EXAMPLE 1

General Materials and Methods

All reagents were purchased from SIGMA CHEMICAL CO., St. Louis, Mo., unless otherwise indicated. DNA manipulations reagents and techniques.

Restriction endonucleases and T4 ligase were obtained from Gibco-BRL. Agarose gel electrophoresis and plasmid DNA preparations were performed according to published procedures (Sambrook, J., E. F. Fritsch, and T. Maniatis, 1989, Molecular cloning: a Laboratory Manual, 2nd ed. Cold Spring Harbor, N.Y.: Cold Spring Harbor Laboratory). Recombinant plasmids containing *P. aeruginosa* mraY were propagated in *E. coli* DH5α (GIBCO-BRL, Rockville, Md.) prior to protein expression in *E. coli* BL21(DE3)/plysS (NOVAGEN, Madison, Wis.). SDS-PAGE was performed with precast gels (NOVAGEN). DNA sequences were determined using an automated ABI PRISM™ DNA sequencer (PERKIN-ELMER ABI, Foster City, Calif.).

EXAMPLE 2

Cloning of *Pseudomonas aeruginosa* mraY

Genomic DNA from *P. aeruginosa* (strain MB4439) was prepared from 100 ml late stationary phase culture in Brain Heart Infusion broth (DIFCO, Detroit, Mich.). Cells were washed with 0.2 M sodium acetate, suspended in 10 ml of TEG (100 mM Tris, pH 7, containing 10 mM EDTA and 25% glucose) and lysed by incubation with 200 μg of N-acetylmuramidase (SIGMA) for 1 h at 37° C. Chromosomal DNA was purified from the cell lysate using a QIAGEN (Santa Clarita, Calif.) genomic DNA preparation kit following the manufacturers' protocol. Briefly, the cell lysate was treated with protease K at 50° C. for 45 min, loaded onto an equilibrated QIAGEN genomic tip, and entered into the resin by centrifugation at 3000 rpm for 2 min. Following washing the genomic tip, the genomic DNA was eluted in distilled water and kept at 4° C. Approximately 50 ng genomic DNA was used as a template in PCR reactions to clone mraY.

Two oligonucleotide primers (GIBCO/BRL, Bethesda, Md.) complementary to sequences at the 5' and the 3' ends of *P. aeruginosa* mraY were used to clone this gene using KLENTAQ ADVANTAGE™ polymerase (CLONTECH, Palo Alto, Calif.). The primer nucleotide sequences were as follows: 5'-TT CAT ATG CTC CTG CTG CTG GCC GAA TAC-3, (SEQ ID NO:3) and 5'-TT GGA TCC TCA ACG CAG CTT CAA GGT G-3' (SEQ ID NO:4). A PCR product representing *P. aeruginosa* mraY was verified by nucleotide sequence, digested with NdeI and BamHI, and cloned between the NdeI and BamHI sites of pET-11a, creating plasmid pPaeMraY. This plasmid was used for expression of the mraY gene in *E. coli*.

EXAMPLE 3
Overexpression and Enzymatic Activity of *Pseudomonas aeruginosa* MraY mraY was cloned into the expression vector pET-11a (NOVAGEN) as described above to create plasmid pPaeMraY. The pET-11a vector allows expression of authentic, non-fusion, proteins. The pET (Plasmids for Expression by T7 RNA polymerase) plasmids are derived from pBR322 and designed for protein over-production in *E. coli*. The vector pET-11a contains the ampicillin resistance gene, and ColE1 origin of replication, in addition to T7 phage promoter and terminator. The T7 promoter is recognized by the phage T7 RNA polymerase but not by the *E. coli* RNA polymerase. A host *E. coli* strain such as BL21(DE3)pLysS is engineered to contain integrated copies of T7 RNA polymerase under the control of lacUV5 that is inducible by IPTG. Production of a recombinant protein in the *E. coli* strain BL21(DE3)pLysS occurs after expression of T7RNA polymerase is induced.

The pPaeMraY plasmid was introduced into the host strain BL21 DE3/pLysS (NOVAGEN) for expression of MraY. Colonies were grown at 37° C. in 100 ml of LB broth containing 100 mg/ml ampicillin and 32 μg/ml chloramphenicol. When cultures reached a cell density of $A_{600}$=0.5, cells were pelleted and then resuspended in M9ZB medium (NOVAGEN) containing 1 mM IPTG. Cells were induced for 3 h at 30° C., pelleted at 3000 g, and frozen at −80° C.

Cultures containing either the recombinant plasmid pPaeMraY or the control plasmid vector, pET-11a, were grown at 30° C. and induced with IPTG. Lysates of cells transformed with pPaeMraY exhibited some 10.3 fold increase in MraY activity over uninduced cell lysates or induced lysates from cells containing the plasmid vector.

Assay for Activity of MraY Enzyme.

The MraY (translocase I) assay was performed using the butanol extraction method described by Brandish and coworkers (Brandish et al., 1996 *J. Biol. Chem.* 271(13) :7609–7614). The assay was performed at room temperature with assay components held at concentrations of: 100 mM TRIS, pH 7.5; 30 mM $MgCl_2$; 60.2 nCi [$^{14}$C]UDP-MurNAc-pentapeptide (14 μM); 40 μM Decaprenol phosphate (SIGMA CHEMICAL CORP.); 0.15% Triton X-100 (w/v); and 100 mg/mL phosphatidyl glycerol SIGMA CHEMICAL CORP.). Enzyme concentration was varied in order to obtain linear kinetics. Aliquots (50 μl) were removed at varying time points and transferred to a fresh tube containing 50 μl of 6M pyridinium acetate, pH 4.2. The mixture was then extracted with 100 μl butanol and 50 μl water. After brief centrifugation, 80 μl of the top butanol layer was quantitated in a Packard TriCarb PACKARD TRICARB™ scintillation counter to determine the amount of Lipid I product produced.

Table 1

Specific Activity of Recombinant MraY from *P. aeruginosa*.

TABLE 1

Specific activity of recombinant MraY from *P. aeruginosa*.

| Recombinant MraY | Specific Activity | Fold Increase in Specific Activity |
| --- | --- | --- |
| *P. aeruginosa* mraY in pET-11a vector | 1428.2 | 10.3 |
| Host *E. coli* cells containing pET-11a (empty vector-Control) | 139.3 | 1 |

---

What is claimed:

1. An isolated polynucleotide selected from the group consisting of:
   (a) a polynucleotide encoding a polypeptide having the amino acid sequence of SEQ ID NO: 2; and
   (b) a polynucleotide consisting of the nucleic acid sequence set forth in SEQ ID NO:1.

2. An expression vector comprising the polynucleotide according to claim 1.

3. An isolated host cell comprising the expression vector of claim 2.

* * * * *